United States Patent [19]

Carpentier et al.

[11] Patent Number: 5,207,218
[45] Date of Patent: May 4, 1993

[54] IMPLANTABLE PULSE GENERATOR

[75] Inventors: Alain Carpentier, Paris, France; Antoine Camps, Eys; Robert Leinders, Gubbecoven, both of Netherlands

[73] Assignee: Medtronic, Inc., Minneapolis, Minn.

[21] Appl. No.: 661,786

[22] Filed: Feb. 27, 1991

[51] Int. Cl.$^5$ .............................................. A61N 1/05
[52] U.S. Cl. .............................................. 128/419 PG
[58] Field of Search ............ 128/419 PG, 419 P, 421, 128/423, 419 F

[56] References Cited

U.S. PATENT DOCUMENTS

| | | | |
|---|---|---|---|
| 3,683,932 | 8/1972 | Cole | 128/419 P |
| 3,842,843 | 10/1974 | Mourot et al. | 128/419 P |
| 3,908,668 | 9/1975 | Bolduc . | |
| 4,144,891 | 3/1979 | Lysfjord et al. | 128/419 P |
| 4,254,775 | 3/1981 | Langer . | |
| 4,262,673 | 4/1981 | Kinney et al. | 128/419 P |
| 4,289,144 | 9/1981 | Gilman | 128/419 P X |
| 4,314,562 | 2/1982 | Ware . | |
| 4,411,268 | 10/1983 | Cox . | |
| 4,445,511 | 5/1984 | Cowdery et al. | 128/419 P |
| 4,735,205 | 4/1988 | Chachques et al. . | |
| 5,070,605 | 12/1991 | Daglow et al. | 128/419 P X |

OTHER PUBLICATIONS

"The Impact of Pending Technologies on a Universal Connector Standard" by Doring et al., published in PACE, vol. 9, pp. 1186-1190.

*Primary Examiner*—Lee S. Cohen
*Assistant Examiner*—Samuel Gilbert
*Attorney, Agent, or Firm*—Reed A. Duthler; Harold R. Patton

[57] ABSTRACT

An implantable pulse generator particularly adapted for implantation in the abdomen. The pulse generator displays a generally flattened configuration having two generally opposed major surfaces and a smaller, circumferential edge surface, and includes a plurality of electrical connectors located in a connector module mounted to one of the major surfaces of the pulse generator. The housing of the pulse generator contains a hybrid circuit mounted generally parallel to the major surfaces of the pulse generator, connected to the electrical connectors by means of feedthroughs passing through one of the major surfaces of the pulse generator, located adjacent to the edges of the hybrid circuit and perpendicular thereto.

9 Claims, 2 Drawing Sheets

IMPLANTABLE PULSE GENERATOR

BACKGROUND OF THE INVENTION

This invention relates generally to medical electrical stimulators, more particularly to muscle stimulators for functional electrical stimulation, and most particularly to implantable electrical stimulators for stimulation of muscle employed as a myocardial substitute.

U.S. Pat. No. 4,735,205 issued to Chachques et al discloses method and apparatus for employing the latissimus dorsi muscle to assist cardiac function. This patent is incorporated herein by reference in its entirety. In the method disclosed in this patent, the latissimus dorsi muscle is surgically resected, divided into two parts to cover the surface of the heart, and inserted into the thoracic cavity by means of a resection of the second rib. After or before positioning the muscle, stimulating electrodes are threaded into the muscle at desired locations to affect contraction of the muscle. Stimulating pulses are provided by an implanted pulse generator, preferably implanted subcutaneously in the abdomen. A pulse generator appropriate for such use is disclosed in U.S. Pat. No. 4,411,268 issued to Cox. Timing of contractions of the latissimus dorsi muscle is controlled by the stimulator, which senses natural contractions of the heart, and stimulates the latissimus dorsi muscle to contract in synchrony therewith. Sensing of heart activity, and stimulation of heart contractions in the absence of underlying heart activity is accomplished by means of an additional electrical lead, coupling the heart to the pulse generator.

The pulse generator disclosed in the above cited patent, like most implantable pulse generators, has a generally flattened external configuration with two major, generally planar surfaces and a circumferential edge surface. Mounted to the circumferential edge surface is a connector block which includes receptacles for each of the three illustrated stimulation leads. This pulse generator is implanted with its major surfaces generally parallel to the skin.

SUMMARY OF THE INVENTION

When implanting a pulse generator in the abdominal region, a relatively limited area is available for implant of the device. As such, the length and width of the pulse generator (length and width of the major surfaces of the pulse generator) are more critical than the thickness of the pulse generator. As additional leads are added to the system illustrated in the Chachques et al patent, either to accomplish sequential stimulation of different muscle portions or to accomplish dual chamber pacing and sensing of the heart, the volume of the connector block increases proportionately. For practical reasons, implantable pulse generators have now evolved to the point where they almost all uniformally take the form of a hermetically sealed metal enclosure, with a molded connector module attached thereto. Connection between the circuitry and battery within the hermetic enclosure and the connector module is typically accomplished by means of feedthroughs.

The inventors of the present application have determined that by relocation of the molded connector module assembly to the major surface of the hermetic enclosure, from the edge surface, a pulse generator is produced that is more readily implanted in the abdominal region, and which can easily accommodate a multiplicity of stimulation and sensing leads. In addition, the inventors have determined that the configuration of the stimulator disclosed herein provides advantages in construction of the stimulator and in connecting the circuitry therein to the electrical connectors within the connector module. These advantages are also of benefit in pulse generators intended for pectoral implant. Feedthroughs are located in two spaced rows along one major surface of the hermetic enclosure, with the circuitry located between the rows of feedthroughs. This is particularly desirable where double sided hybrid circuitry is located, in that it allows for simple interconnection of either side of the hybrid to the feedthrough pins, without the necessity of bending and routing elongated feedthrough pins, as would be required if the connector module were located along an edge surface of the hermetic enclosure. Provision of the feedthrough pins perpendicular to the plane of the hybrid circuitry and arrayed along two edges of the hybrid circuitry simplifies the interconnection of the hybrid circuitry to the electrical connectors within the connector module and provides increased flexibility in hybrid circuit layouts.

DETAILED DESCRIPTION OF THE INVENTION

Figure 1:
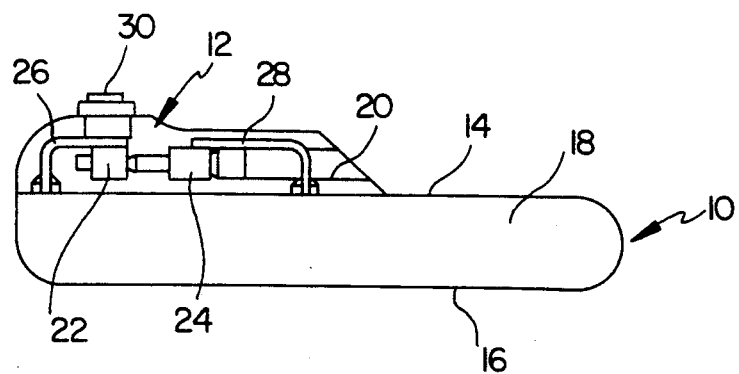
FIG. 1 is a side, plan view of a pulse generator according to the present invention.

FIG. 1 is a side, plan view of a pulse generator according to the present invention. The structure of the pulse generator illustrated can be divided into two major assemblies. Contained within the metal hermetic enclosure 10 is the battery and circuitry of the pulse generator. The enclosure 10, seen in this view from the side or edge, displays a generally flattened configuration with two large, generally planar major surfaces 14 and 16 and a circumferential edge surface 18. In order to provide a more biocompatible configuration, the corners connecting the side and edge surfaces are generally rounded.

The second major assembly is the connector module 12, which is molded from a transparent plastic, typically epoxy. Visible through the transparent epoxy is the structure associated with the outer most connector receptacle. The connector receptacle takes the form of a stepped cylindrical bore 20, which may correspond to the IS-1 or VS-1 in-line connector configuration, generally described in the article "The Impact of Pending Technologies on a Universal Connector Standard", by Doring et al, published in PACE, Vol. 9, pp. 1186–1190, incorporated herein by reference in its entirety. This basic connector configuration is now widely in use throughout the cardiac pacemaker industry and is well known to those of skill in the art. Visible through the transparent epoxy are two connectors 22 and 24. These connectors are coupled to the circuitry within hermetic enclosure 10 by means of feedthrough wires 26 and 28, which pass through feedthroughs into the interior of hermetic enclosure 10. Connector 24 employs a crown contact, which is a louvered, cylindrical receptacle with curved, inwardly directed flat strips, illustrated in more detail in FIG. 3. Connector block 22 employs a set screw to make contact with a cylindrical pin on the proximal end of the pacing or muscle stimulation lead. Access to the set screw is obtained by means of a pierceable grommet 30, of the type generally disclosed in U.S. Pat. No. 3,908,668, issued to Bolduc. Connection of the feedthrough wires 26 and 28 to connector blocks 22 and 24 is made by means of a weld or other method of mechanical connection.

Figure 2:
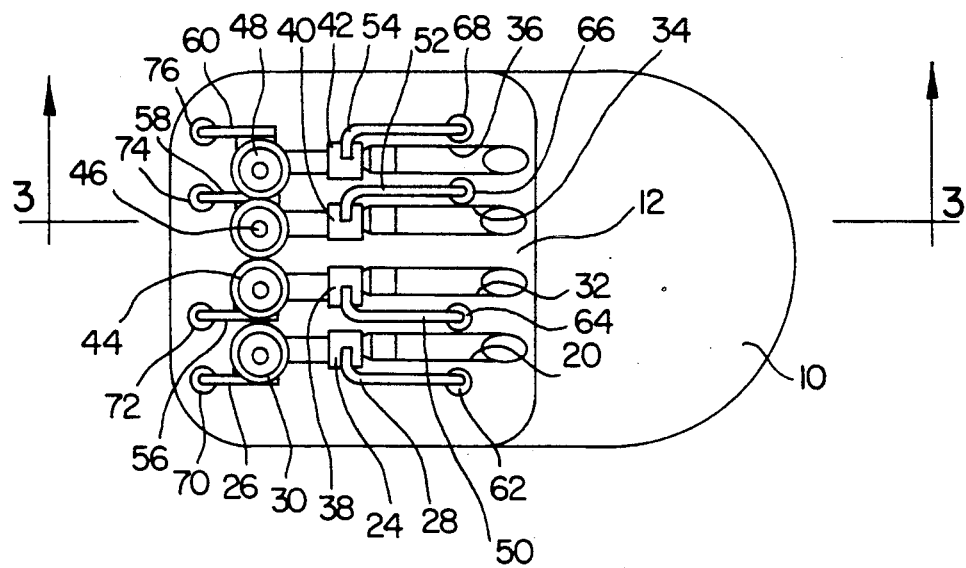
FIG. 2 is a top, plan view of a pulse generator according to the present invention.

FIG. 2 is a top, plan view of the pulse generator illustrated in FIG. 1. In FIG. 2, it is apparent that the connector module is provided with four stepped cylindrical receptacles 20, 32, 34 and 36, each of which has associated therewith a crown contact connector 24, 38, 42, 44 for engaging the connector ring on the proximal end of a pacing or muscle stimulation electrode and a set screw connector block for engaging the connector pin of the corresponding leads. In this view, the connector blocks corresponding to connector block 22 in FIG. 1 are not readily visible as they are obscured by sealing grommets 30, 44, 46 and 48. The configuration of the receptacles 20, 32, 34, 36 may be identical. Alternatively, the receptacles may be differently dimensioned to prevent inadvertent insertion, for example, of a cardiac pacing lead into a receptacle intended for use with a muscle stimulating lead or vice versa.

Figure 3:
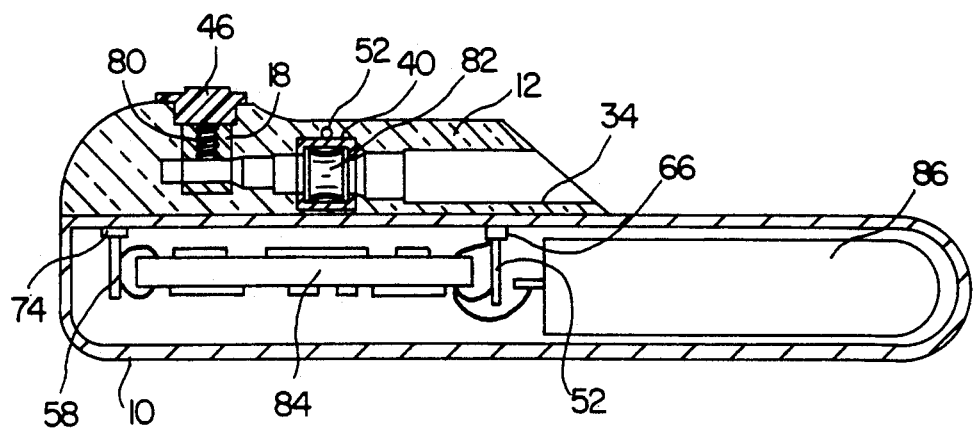
FIG. 3 is a side, cutaway view through the pulse generator illustrated in FIGS. 1 and 2.

In this view, it can be seen that each of the feedthrough wires 28, 50, 52, 54, 26, 56, 58, 60 passes through a feedthrough into hermetic enclosure 10, allowing for contact with the circuitry located therein. Feedthroughs 62, 64, 66, 68, 70, 72, 74 and 76 are arranged generally along two parallel lines. As illustrated in FIG. 3 below, these two parallel lines are located on either side of the hybrid circuitry located within enclosure 10.

FIG. 3 is a side, cutaway view through the pulse generator illustrated in FIGS. 1 and 2, through receptacle 34. In this view, set screw 80 is visible within connector block 78. Access to set screw 80 is obtained by piercing sealing grommet 46 with a screwdriver or hex wrench, as appropriate. Connector 82 is similarly visible within connector block 40.

Within hermetic enclosure 10, the hybrid circuitry 84 and the battery 86 are mounted. These are typically mounted by means of plastic spacers or retainers, which have been omitted in this view for the sake of clarity. Appropriate forms of such retainers or spacers are illustrated in U.S. Pat. No. 4,314,562, issued to Ware, incorporated herein by reference. However, fabrication of appropriately sized and dimensioned plastic retainers will vary depending on the particular configuration of the hybrid circuitry and battery employed. In light of the teaching of the above cited patent, this is now believed to be a matter of routine engineering, readily accomplished by one of skill in the art.

For purposes of the present invention, it is the interrelation of hybrid circuitry 84 and the feedthrough pins 52 and 58 which is of primary importance. As illustrated, connection between the hybrid 84 and the connector pins 58 and 52 may be accomplished by either the upper or the lower side of the hybrid. Having feedthroughs extending along two opposed edges of the hybrid, allows for a substantial increase in flexibility with regard to layout of the printed circuit paths and connectors pads on the hybrid. In contrast to prior art hybrids, which would have only one edge located adjacent the feedthroughs, the present invention provides the ability to locate connector pads along two opposing edges. In addition, placing the connector pins perpendicular to the plane of the hybrid 84 allows for easy access to either the upper or lower side of the hybrid 84.

Placing the feedthrough wires perpendicular to the surface of the hybrid, arrayed along two opposing edges of the hybrid also minimizes the length of the jumper wires required to connect the hybrid to the connector pins, and eliminates any necessity to bend the feedthrough pins or otherwise route them within the hermetic enclosure 10. This is believed to substantially simplify the manufacture of the pulse generator.

Figure 4:
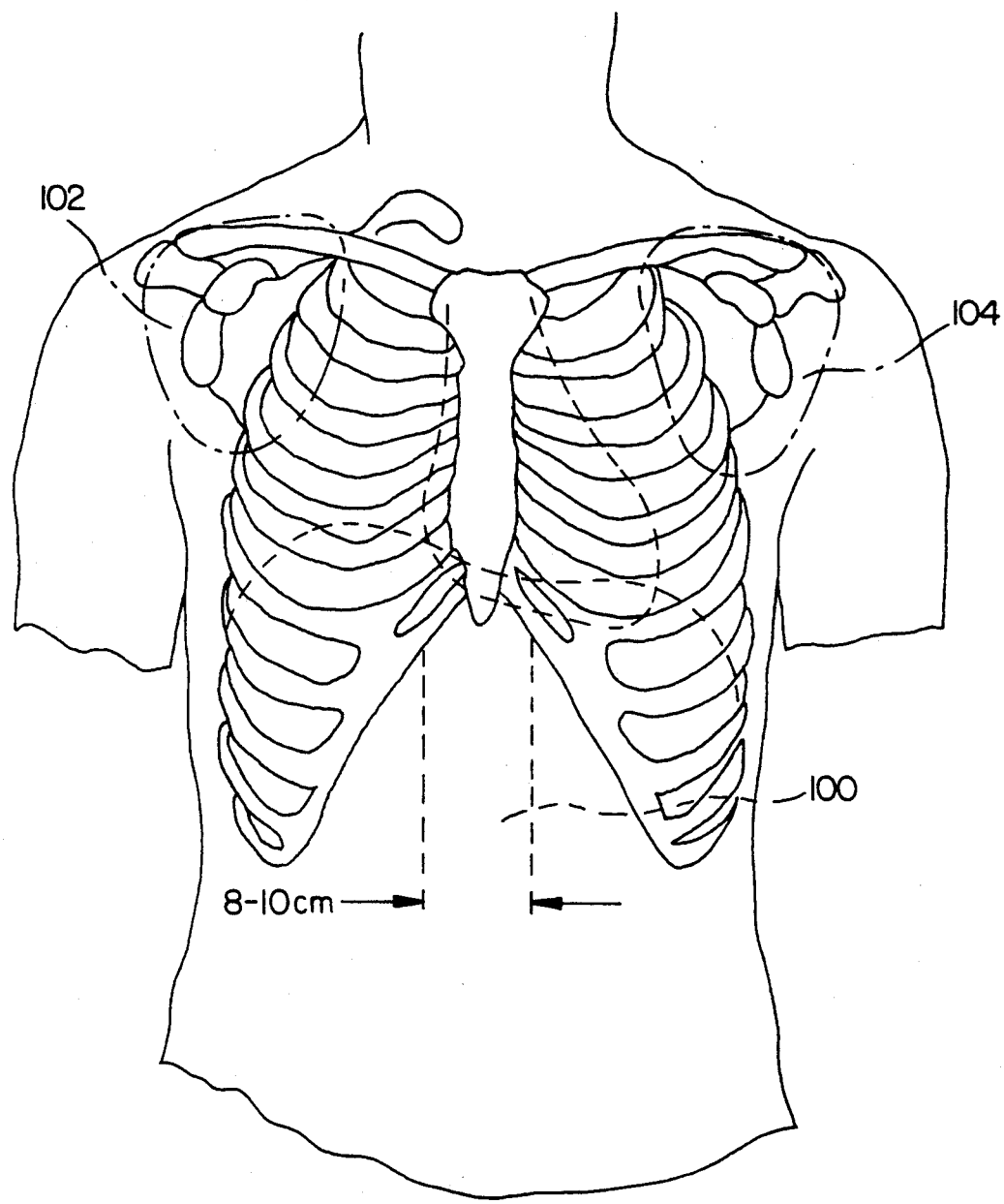
FIG. 4 is a drawing of the thoracic region of the human body, illustrating locations for implant of a pulse generator according to the present invention.

FIG. 4 illustrates a view of the human thorax, illustrated in the areas of implant of the pulse generator. The pulse generator is preferably implanted within abdominal area 100, with the major surfaces 16 and 14 of the hermetic enclosure 10 generally parallel to the skin and to the underlying layers of muscle tissue. Because area 100 is relatively restricted, it is preferable that the outer dimensions of the pulse generator (length and width) do not exceed 7 cm by 5 cm. The pulse generator, in some cases, may be implanted in the pectoralis regions 102, 104.

While the above illustrated embodiment employs a pulse generator which has four lead receptacles, the basic design illustrated is readily adaptable to five or more connector receptacles. Indeed, as the number of desired connector receptacles increases, the value of the basic design configuration also increases. The present invention allows for large numbers of receptacles and associated connectors and feedthroughs with a minimum of increased complexity with regard to the manufacture of the pulse generator. While the above embodiment is particularly adapted for abdominal implant, in conjunction with a stimulator adapted to stimulate the latissimus dorsi muscle, wrapped around the heart, the basic design configuration is also believed applicable to other forms of implantable pulse generators where large numbers of connector lumens and associated connector blocks and feedthroughs are required to perform complicated stimulation and/or sensing functions.

Furthermore, while the disclosed embodiment employs jumper wires to connect the hybrid circuitry to the feedthroughs, it is anticipated that the invention might also be practiced using feedthrough wires passed through holes in the hybrid substrate and soldered or welded directly to the conductive paths on the hybrid. In such cases, the feedthrough pins might also interconnect the opposite sides of the hybrid. Of course, in this embodiment, the pins need not be limited to areas closely adjacent the edges of the hybrid. As an alternative to welding or soldering, connection between the feedthrough pins and the hybrid circuit may be accomplished mechanically by means of crown contact or other known types of electrical connectors. As such, the above embodiment should be considered exemplary, rather than limiting, with regard to the following claims.

In conjunction with the above disclosure, we claim:
1. An implantable pulse generator, comprising:
a hermetically sealed housing containing a hybrid circuit and a battery, said housing defining two generally planar opposed major surfaces connected to one another by means of a circumferential edge surface, such that said housing displays a generally flattened configuration, said hybrid circuit located generally parallel to said major surfaces of said housing; and a connector module mounted to one of said major surfaces of said housing, said connector module comprising a plurality of connector receptacles arranged parallel to said major surfaces and electrical connectors associated with said receptacles, each of said electrical connectors coupled to said hybrid circuit within said housing by means of a feedthrough pin extending through a feedthrough, said feedthrough pins extending through said housing perpendicular to said major surfaces and to said hybrid circuit.

2. An implantable pulse generator according to claim 1 wherein said feedthroughs and feedthrough pins are arranged adjacent opposite edges of said hybrid circuit.

3. A pulse generator according to claim 1 or claim 2 wherein each of said receptacles has associated therewith at least two of said electrical connectors.

4. A pulse generator according to claim 3 wherein said feedthroughs are arranged generally along two parallel lines, located adjacent opposite edges of said hybrid circuit, and wherein each of said electrical connectors associated with one of said receptacles is coupled to a said feedthrough pin passing through a said feedthrough in a different one of said two generally parallel lines of said feedthroughs.

5. An implantable pulse generator according to claim 1 wherein said hybrid circuit is coupled to said feedthrough pins by means of jumper wires.

6. An implantable pulse generator according to claim 1 wherein said receptacles within said connector module are differentiated from one another by size whereby inadvertent misconnection of electrical leads with said pulse generator may be avoided.

7. An implantable pulse generator, comprising:

a hermetically sealed housing containing an electrical circuit and a battery, said housing defining two generally planar opposed major surfaces connected to one another by means of a circumferential edge surface, such that said housing displays a generally flattened configuration, said electrical circuit located generally parallel to said major surfaces of said housing;

a connector module mounted to one of said major surfaces of said housing, said connector module comprising a plurality of connector bores arranged parallel to said major surfaces each having opening to an exterior surface of said connector module and a first and a second electrical connector associated with each said connector bore, said first electrical connectors located closer to the openings of said connector bores than said second electrical connectors; and a plurality of feedthroughs, mounted to said one of said major surfaces of said housing, each of said feedthroughs coupled to one of said electrical connectors and to said electrical circuit, said feedthroughs being arranged generally along parallel first and second lines located adjacent opposite edges of said electrical circuit.

8. A pulse generator according to claim 7 wherein said first electrical connectors are each coupled to one of said feedthroughs located along said first line and said second electrical connectors are each coupled to one of said feedthroughs located along said second line.

9. A pulse generator according to claim 7 or claim 8 wherein said connector bores are parallel to one another within said connector module and wherein said first and second electrical connectors are located generally along two parallel lines.

* * * * *